US005360415A

United States Patent [19]
Yabushita et al.

[11] Patent Number: 5,360,415
[45] Date of Patent: Nov. 1, 1994

[54] ANTI-INFECTIVE CATHETER

[75] Inventors: Yasunori Yabushita, Kyoto, Japan; Hiroshi Yokoi, Troy, N.Y.; Masanao Koyama; Munehiro Takatsuka, both of Kyoto, Japan

[73] Assignee: Unitika Ltd., Hyogo, Japan

[21] Appl. No.: 804,362

[22] Filed: Dec. 10, 1991

[51] Int. Cl.$^5$ .................................... A61M 25/00
[52] U.S. Cl. ................................................ 604/265
[58] Field of Search ................ 604/890.1, 266, 265, 604/28, 85, 96, 307

[56] References Cited

U.S. PATENT DOCUMENTS

| | | | |
|---|---|---|---|
| 4,326,532 | 4/1982 | Hammar | 604/266 |
| 4,642,111 | 2/1987 | Sakamoto et al. | 604/890.1 |
| 4,642,267 | 2/1987 | Creasy et al. | 428/413 |
| 5,091,205 | 2/1992 | Fan | 604/266 |
| 5,153,003 | 10/1992 | Kerihara et al. | 604/266 |
| 5,156,601 | 10/1992 | Lorenz et al. | 604/307 |
| 5,158,538 | 10/1992 | Shaw | 604/28 |
| 5,158,548 | 10/1992 | Lau et al. | 604/96 |
| 5,160,320 | 11/1992 | Yum et al. | 604/85 |

FOREIGN PATENT DOCUMENTS 0166998  8/1986  European Pat. Off. .

Primary Examiner—C. Fred Rosenbaum
Assistant Examiner—Manuel Mendez
Attorney, Agent, or Firm—Sughrue, Mion, Zinn, Macpeak & Seas

[57] ABSTRACT

An anti-infective catheter on which a layer of a water absorbing polymer is formed. Since the layer of the water absorbing polymer swells by absorbing body fluid in subcutaneous tissue, space between the inserted catheter and its peripheral skin moiety is filled quickly, thus preventing penetration of pathogens in the living body along the wall of the catheter. The anti-infective catheter of the present invention can be inserted in the living body easily without forming a site for the arrangement of a cuff and can prevent penetration of pathogens immediately after its insertion without affecting peripheral tissue.

8 Claims, No Drawings

ANTI-INFECTIVE CATHETER

FIELD OF THE INVENTION

This invention relates to an anti-infective catheter suitable for use in dialysis, central venous alimentation and the like.

BACKGROUND OF THE INVENTION

In many cases when catheterization is performed for a prolonged period of time, pathogens penetrate into the living body via the catheter. This is especially in the case of a catheter dwelling in a blood vessel. Once penetrated, pathogens intrude into every part in the body thereby, causing serious problems.

With the aim of preventing or reducing pathogenic infection caused by the use of a catheter, three techniques have mainly been used; namely, (1) containment of a disinfectant in a base material of the catheter, (2) coating of the surface of the catheter with a resin containing a disinfectant and (3) attachment of a cuff to a part of the body where a catheter is to be embedded. When a disinfectant is used in the case of techniques (1) and (2), the disinfectant exudes from a catheter and imparts its germicidal effect in the surface area of the catheter. When a cuff is used in the case of (3), peripheral tissue enters into the cuff and develops therein to form a barrier against pathogens, thereby preventing the catheterized part from infection. In some cases, however, use of a catheter containing a disinfectant is rather apt to bring about infection, because the exuded disinfectant from the catheter stimulates peripheral tissue and causes inflammation. In the case of the attachment of a cuff, the infection preventing effect cannot be expected until peripheral tissue develops inside the cuff. In addition, there is a complexity due to the necessity of forming a cuff-arranging part at the inserting part of the catheter.

SUMMARY OF THE INVENTION

The object of this invention resides in providing an anti-infective catheter which comprises a catheter and a water absorbing polymer, wherein a layer of the water absorbing polymer is formed on at least the surface of the portion of the catheter to be maintained in the living body.

The catheter of the present invention can be inserted into the living body easily because it is not necessary to perform an extra incision, which is essential for cuff embedding. Also, the catheter of the present invention is free from disinfectant-originating side-effects because the catheter does not require a disinfectant. Further, the catheter of the present invention can prevent penetration of pathogens starting immediately after its insertion, since it swells quickly by absorbing body fluid. As a consequence, the catheter of the present invention is especially useful when it is used as a catheter which requires a prolonged period of indwelling time, such as a catheter for use in dialysis, central venous alimentation or the like.

DETAILED DESCRIPTION OF THE INVENTION

The present invention is characterized in that a layer of a water absorbing polymer is formed on the surface of at least a portion of a catheter, i.e., the portion which is located under subcutaneous tissue in the living body where the catheter is intended to be subjected to indwelling. The layer of the water absorbing polymer swells by absorbing body fluid under the skin and completely fills the space between the catheter and biological tissue, thereby preventing penetration of pathogens into the living body along the outer surface of the catheter.

Illustrative examples of the water absorbing polymer of the present invention include for instance: chitin; polyacrylate; copolymers containing acrylic acid such as a starch-acrylic acid graft copolymer, a vinyl acetate-acrylic acid copolymer and the like; copolymers containing acrylonitrile such as a cellulose-acrylonitriie graft copolymer, a starch-acrylonitrile graft copolymer, a hydrolyzed product of polyacrylonitrile and the like; polyvinyl alcohol; copolymers containing vinyl alcohol such as a vinyl alcohol-maleic anhydride copolymer, a vinyl alcohol-vinylacetate copolymer and the like; copolymers containing maleic anhydride such as an isobutylene-maleic anhydride copolymer, a styrene-maleic anhydride copolymer, a methylvinylether-maleic anhydride copolymer and the like; and carboxymethylated cellulose products such as a carboxymethyl cellulose, a carboxymethyl rayon and the like. These water absorbing polymers may be in the form of salts such as chlorides, sulfates, sodium salts, calcium salts and the like. A chitin material eligible for use in the present invention may be not only the naturally existing poly-$\beta$-1,4-N-acetylglucosamine, but, also a deacetylation product of the poly-$\beta$-1,4-N-acetylglucosamine (a deacetylation degree of from 1 to 80%) or a product having a high deacetylation degree (a deacetylation degree of 80% or more) generally called chitosan.

The water absorbing polymer to be used in the present invention may be selected from the above described compounds singly or as a mixture of two or more, which may be mixed further with other synthetic polymer compounds, such as ethylene-vinyl acetate copolymer, polyethylene, polypropylene, polyurethane, polyester, nylon, silicone resin, polyvinyl chloride and the like, with the aim of increasing moldability at the time of molding into a suitable form. As a consequence, the term "water absorbing polymer" as used herein is intended to include not only the water absorbing polymer itself but also its mixture with other types of polymers.

When the anti-infective catheter of the present invention is prepared, formation of a water absorbing polymer layer on the surface of a catheter may be effected, for example, by fixing a suitable form of a water absorbing polymer by means of thermal welding, adhesion making use of an adhesive or the like, or by dissolving a water absorbing polymer in an organic solvent, particularly one with high polarity such as N,N-dimethylacetamide, N,N-dimethylformamide, dimethylsulfoxide, tetrahydrofuran, an alcohol and a halogenated hydrocarbon, and coating the solution on the surface of the intended portion of the catheter. The water absorbing polymer layer may be formed on any indwelling portion of the catheter under the skin, preferably a portion which is located in subcutaneous tissue close to the skin but not inside a blood vessel. The water absorbing polymer layer may be in any shape or size, provided that it remains under the skin when swelled, but the layer may preferably be formed in a cylindrical shape having a thickness of from 0.01 to 20 mm, preferably from 0.1 to 10 mm, and a width of from 1 to 50 mm, preferably from 5 to 30 mm, on the peripheral surface of the catheter. When a suitable shape of a water absorbing polymer is fixed to a catheter to form such a layer, the water absorbing polymer may be made into a film, a sheet, a non-woven fabric, a sponge, a thread, a tube or the like. A water absorbing polymer in the shape of a film, a sheet, a non-woven fabric or a sponge may be cut into a rectangular form with a width of from 1 to 50 mm, preferably from 5 to 30 mm, coated with an adhesive such as a cyanoacrylate type adhesive, an urethane type adhesive and an epoxy type adhesive, and then wound round a catheter until a preferred thickness of the layer is obtained. A water absorbing polymer in the shape of a thread may be coated with an adhesive and then wound round a catheter until preferred thickness and width of the layer are obtained. In the case of a water absorbing polymer in the shape of a tube, the polymer may be molded into a cylindrical shape with a wall thickness of from 0.01 to 20 mm, preferably from 0.1 to 10 mm, and a length of from 1 to 50 mm, preferably from 5 to 30 mm, having such an inside diameter that a catheter can be inserted into the tube and inner surface of the tube and outer surface of the catheter adhere to each other. Fixing of such materials may also be effected by thermal welding without using an adhesive.

The catheter to be used in the present invention may be any tube made of a synthetic polymer such as ethylene-vinyl acetate copolymer, polyethylene, polypropylene, polyurethane, polyester, nylon, silicone resin, polyvinyl chloride or the like, provided that it can be inserted in the living body for the purpose of performing discharge of body fluid, circulation of body fluid, injection or discharge of infusion or perfusion solution, inspections and the like.

Examples of the present invention are given below by way of illustration and not by way of limitation.

EXAMPLE 1 AND COMPARATIVE EXAMPLE 1

A sheet having a thickness of 1 mm and a width of 2 cm, which has been prepared in advance from 80 parts of a carboxymethyl rayon and 20 parts of an ethylene-vinyl acetate copolymer, was adhered to a polyurethane catheter (outer diameter, 2mm; length, 30 cm) at a position 20 cm distant from its tip, by winding the sheet round the catheter using a cyano-acrylate adhesive. A portion of the thus prepared catheter (23 cm in length from its tip) was subjected to catheterization in subcutaneous tissue under a hair-cropped dorsal part of a rabbit (body weight, about 2.5 kg). The insertion hole of the catheter was covered with a piece of absorbent cotton which had been soaked with 1 ml cell suspension of *Staphylococcus aureus,* 1 ml cell suspension of *Staphylococcus epidermidis* and 1 ml cell suspension of *Candida albicans,* each suspension containing $10^8$ cells. The cotton piece was fixed with a piece of tape. Ten days later, the catheter was removed by incising the skin. It was found that the coated sheet had swelled to about three times its original thickness. The thus removed catheter was cut out at an interval of 2 cm, and each of the cut pieces was put on brain/heart infusion agar medium (manufactured by Becton Dickinson and Company) and incubated under appropriate conditions. As the results, $2 \times 10^3$ colonies per piece were found with respect to the pieces cut out from the catheter portion outside the coated sheet, while none of the pieces cut out from the inside portion from the sheet-coated part to the tip part showed formation of colonies.

As a comparative example, the same experiment was carried out except that the polyurethane catheter was used without adhering the carboxymethyl rayon sheet. As a result, bacteria were detected from every piece cut out from the inserted portion of the catheter, even from the tip part of the catheter, with a frequency of $2 \times 10^2$ colonies per piece.

EXAMPLE 2

A vinyl acetate-methyl acrylate copolymer prepared by polymerizing methyl acrylate with vinyl acetate was subjected to saponification with sodium hydroxide to obtain a film of a vinyl alcohol-acrylic acid copolymer. The thus obtained film with a width of 2 cm was wound round the same polyurethane catheter as used in Example 1 using a cyano-acrylate adhesive until the film layer become a thickness of 1 mm. When the resulting catheter was soaked in water for 5 minutes, the film of the vinyl alcohol-acrylic acid copolymer swelled to about five times its original thickness.

EXAMPLE 3

A non-woven fabric made of chitosan was attached to a polyvinyl chloride catheter in the same manner as in Example 2. When the resulting catheter was soaked in water for 5 minutes, the layer of the non-woven fabric swelled to about three times its original thickness.

EXAMPLE 4

Eighty (80) parts of a starch-acrylamide polymer prepared by polymerizing starch with acrylamide, was mixed thoroughly with 20 parts of an ethylene-vinyl acetate copolymer at 80° C. The mixture was molded into a sheet of 0.8 mm in thickness. The thus obtained sheet was attached to a polyurethane catheter in the same manner as in Example 2. When the resulting catheter was soaked in water for 5 minutes, the sheet layer swelled to about three times its original thickness.

EXAMPLE 5

A mixture prepared at 80° C. from 60 parts of chitosan powder (deacetylation degree, 85%) and 40 parts of an ethylene-vinyl acetate copolymer was molded into a tubular shape having an outer diameter of 4 mm and an inner diameter of 2.2 mm, and the tube was cut out to a length of 30 mm to obtain a cylindrical form of a molded product. The thus obtained cylindrical product was adhered to a catheter of 2 mm in outer diameter and 30 cm in length, at a position 20 cm from the tip of the catheter, using a cyano-acrylate adhesive. In this way, a catheter having a layer of a water absorbing polymer was obtained.

Thus, it is apparent that there has been provided, in accordance with the present invention, an anti-infective catheter which comprises a catheter and water absorbing polymer wherein a layer of the water absorbing polymer is formed on the surface of at least portion of the catheter to be maintained in the living body.

Although some preferred embodiments have been described, many modifications and variations may be made thereto in the light of the above teachings. It is therefore to be understood that within the scope of the appended claims, the invention may be practiced otherwise than as specifically described.

While the invention has been described in detail and with reference to specific examples thereof, it will be apparent to one skilled in the art that various changes and modifications can be made therein without departing from the spirit and scope thereof.

What is claimed is:

1. An anti-infective catheter which comprises a catheter and a water absorbing polymer selected from the group consisting of chitin, polyacrylic acid, copolymers containing acrylic acid, copolymers containing acrylonitrile, polyvinyl alcohol, copolymers containing vinyl alcohol, copolymers containing maleic anhydride and carboxymethylated cellulose products, and mixtures thereof, wherein a layer of said water absorbing polymer having a thickness of from 0.01 mm to 20 mm and a width of from 1 to 50 mm is formed on the outer surface of at least a portion of said catheter to be maintained in the living body.

2. The anti-infective catheter according to claim 1, wherein said chitin is selected from the group consisting of poly-$\beta$-1,4-N-acetylglucosamine and a deacetylation product of poly-$\beta$-1,4-N-acetylglucosamine.

3. The anti-infective catheter according to claim 1, wherein said copolymer containing acrylic acid is selected from the group consisting of starch-acrylic acid graft copolymer and vinylacetate-acrylic acid copolymer.

4. The anti-infective catheter according to claim 1, wherein said copolymer containing acrylonitrile is selected from the group consisting of cellulose-acrylonitrite graft copolymer, starch-acrylonitrile graft copolymer and a hydrolyzed product of polyacrylonitrile.

5. The anti-infective catheter according to claim 1, wherein said copolymer containing vinyl alcohol is selected from the group consisting of vinyl-alcohol-maleic anhydride copolymer and vinyl alcohol-vinylacetate copolymer.

6. The anti-infective catheter according to claim 1, wherein said copolymer containing maleic anhydride is selected from the group consisting of isobutylene-maleic anhydride copolymer, styrene-maleic anhydride copolymer and methylvinylether-maleic anhydride copolymer.

7. The anti-infective catheter according to claim 1, wherein said carboxymethylated cellulose product is selected from the group consisting of carboxymethyl cellulose and carboxymethyl rayon.

8. The anti-infective catheter according to claim 1, wherein said water absorbing polymer comprises a mixed composition of at least two different water absorbing polymers.

* * * * *